US007008408B2

(12) United States Patent
Otsubo

(10) Patent No.: US 7,008,408 B2
(45) Date of Patent: Mar. 7, 2006

(54) DISPOSABLE BODY FLUID ABSORBENT WEARING ARTICLE

(75) Inventor: Toshifumi Otsubo, Kagawa-ken (JP)

(73) Assignee: Uni-Charm Corporation, Ehime-Ken (JP)

( * ) Notice: Subject to any disclaimer, the term of this patent is extended or adjusted under 35 U.S.C. 154(b) by 422 days.

(21) Appl. No.: 10/067,334

(22) Filed: Feb. 7, 2002

(65) Prior Publication Data
US 2003/0004483 A1    Jan. 2, 2003

(30) Foreign Application Priority Data
Feb. 7, 2001  (JP) ............................. 2001-031553

(51) Int. Cl.
*A61F 13/15* (2006.01)
(52) U.S. Cl. ............................. 604/385.01; 604/385.26
(58) Field of Classification Search ........... 604/385.01, 604/385.19, 385.101, 379–380, 385.21–385.28
See application file for complete search history.

(56) References Cited

U.S. PATENT DOCUMENTS

| 5,382,246 | A | * | 1/1995 | Kawano | ................ | 604/385.24 |
| 5,558,660 | A | * | 9/1996 | Dreier | ................... | 604/385.19 |
| 5,575,785 | A | * | 11/1996 | Gryskiewicz et al. | .. | 604/385.28 |
| 5,601,544 | A | * | 2/1997 | Glaug et al. | ........... | 604/385.28 |
| 5,792,130 | A | | 8/1998 | Widlund et al. | | |
| 6,152,908 | A | * | 11/2000 | Widlund et al. | ........ | 604/385.19 |
| 6,159,191 | A | * | 12/2000 | Mishima et al. | ........ | 604/385.28 |
| 6,645,186 | B1 | * | 11/2003 | Otsubo | .................. | 604/385.01 |
| 6,702,799 | B1 | * | 3/2004 | Otsubo | .................. | 604/385.21 |
| 2002/0029029 | A1 | * | 3/2002 | Otsubo | ................ | 604/385.101 |

FOREIGN PATENT DOCUMENTS

| EP | 0763353 | 3/1997 |
| EP | 09669940 | 12/1999 |
| EP | 0990433 | 4/2000 |
| EP | 0990434 | 4/2000 |
| EP | 1034760 | 9/2000 |
| EP | 1057463 | 12/2000 |
| JP | 7-112003 | 5/1995 |
| JP | 7-15534 | 6/1995 |

* cited by examiner

*Primary Examiner*—Michele M. Kidwell
(74) *Attorney, Agent, or Firm*—Lowe Hauptman & Berner, LLP

(57) ABSTRACT

A disposable body fluid absorbent wearing article includes a body fluid absorbent pad. A crotch region of the pad is formed on its transversely opposite sides with a pair of darts extending in a longitudinal direction of the article. The pad has a liquid-absorbent core including a central core section lying between the darts and lateral core sections lying outside the respective darts. The central and lateral core sections are contiguous to each other in a region beyond forward or rearward the darts. The respective lateral core sections and respective side flaps form therebetween pockets opening inwardly of the pad.

22 Claims, 8 Drawing Sheets

DISPOSABLE BODY FLUID ABSORBENT WEARING ARTICLE

BACKGROUND OF THE INVENTION

This invention relates to a disposable body fluid absorbent wearing article such as a disposable diaper.

Japanese Patent Application No. 1995-112003A discloses a disposable absorbent pad comprising a pad itself and an elastic waist band. This absorbent pad comprises a liquid-pervious topsheet, a liquid-impervious backsheet and a liquid-absorbent core disposed between these two sheets wherein respective end regions of end flaps extending outward beyond longitudinally opposite ends of the core are connected to the elastic waist band. The absorbent pad is formed with side flaps transversely extending from the pad and being elastically stretchable in longitudinal direction thereof. These side flaps are folded back at least partially in the longitudinal direction toward the inner side of the absorbent pad. This absorbent pad of well known art is described to ensure that the pad itself comes in close contact with the wearer's skin between groins of the wearer's thighs as the elastic waist band is put around the wearer's waist.

Japanese Patent Application No. 1995-155344A discloses disposable pants comprising a stretchable pants-member and a pad member. The pad member comprises a liquid-pervious topsheet, a liquid-impervious backsheet and a liquid-absorbent core disposed between these two sheets wherein end flaps and side flaps extend from longitudinally opposite ends and transversely opposite side edges, respectively. Front and rear end regions of the end flaps are fixed to the pants-member in the vicinity of the waist line. The side flaps are elastically stretchable in the longitudinal direction and form a pair of pockets opening inwardly of the pad member. Such disposable pants are described to ensure that the pad member comes in close contact with the wearer's skin between groins of the wearer's thighs as the pants-member is put on the wearer's body.

The body fluid absorbent pads such as the pad itself disclosed in the Japanese Patent Application No. 1995-112003A and the pad member disclosed in the Japanese Patent Application No. 1995-155344A commonly intend to ensure that the pad comes in close contact with the wearer's skin between the groins of the thighs. To achieve this, a width of the pad in the crotch region, in other words, surface area as well as volume available for absorption of body fluid should be inevitably limited and it may be often difficult for the pad to absorb body fluids rapidly.

SUMMARY OF THE INVENTION

It is an object of this invention to provide a disposable body fluid absorbent wearing article improved so that body fluids can be rapidly absorbed although the width of the body fluid absorbent pad in the crotch region is dimensioned to be relatively narrow.

According to this invention, there is provided a disposable body fluid absorbent wearing article having a front waist region, a rear waist region and a crotch region, comprising a body fluid absorbent pad including a liquid-absorbent core, a casing covering at least a body facing side of the absorbent core and extending outwardly from a circumferencial edge of the core, and a means to retain the body fluid absorbent pad on a wearer's body.

The pad is further formed in its transversely opposite sides in the crotch region with a pair of darts, by folding parts of the casing, in a manner that the pair of darts are opposed to each other and in a shape of circular arcs which are convex toward a center line bisecting a width of the pad. The pad comprises a central core section lying between the pair of darts and lateral core sections lying outside the respective darts so that the central and lateral core sections are contiguous to each other at least one of regions beyond forward and rearward the pair of darts in longitudinal direction of the pad. The core has its outer peripheral edge surrounded by end flaps and side flaps both being contiguous to the casing and extending outward beyond the outer peripheral edge of the core. The side flaps extending outward beyond transversely opposite side edges of the core are folded back toward a body facing surface of the pad and longitudinally opposite end regions of respective side flaps are fixed to the body facing surface so that pockets opening inwardly of the pad are formed between respective the side flaps and respective lateral core sections. The side flaps folded back toward the body facing surface of the pad respectively have body facing side edge regions provided in parallel to the center line with elastic members secured under tension to these inner side edge regions.

DETAILED DESCRIPTION OF THE PREFERRED EMBODIMENTS

Details of a disposable wearing article will be more fully understood from the description of a disposable diaper as one embodiment of this invention given hereunder with reference to the accompanying drawings.

Figure 1:
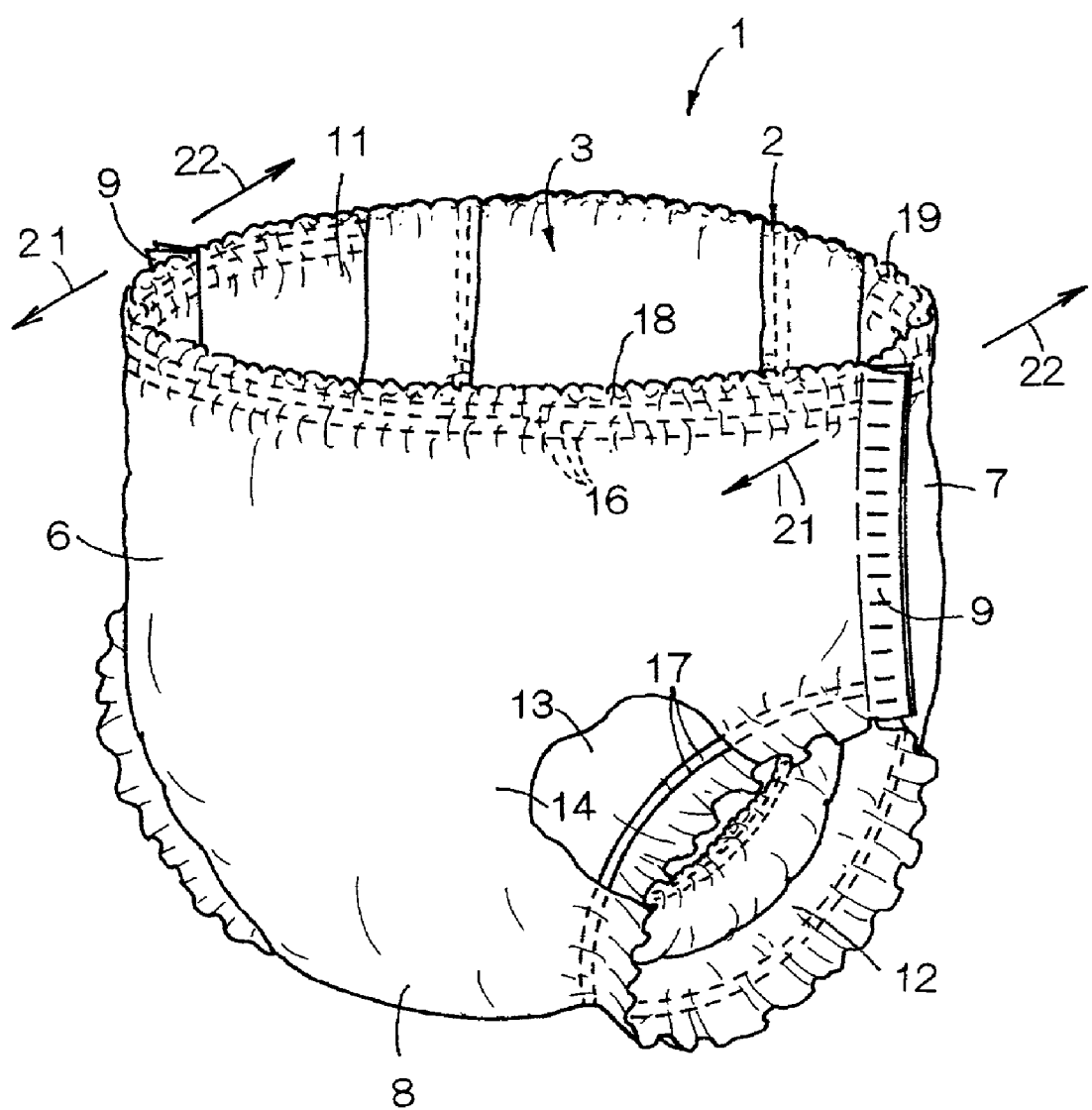
FIG. 1 is a partially cutaway perspective view showing a typical embodiment of the wearing article according to this invention.

A disposable diaper 1 shown by FIG. 1 in a perspective view as partially cutaway basically comprises a cover or chassis 2 of pants-type and a body fluid absorbent pad 3 attached to the inner side of the cover 2. The cover 2 has a front waist region 6, a rear waist region 7 and a crotch region 8. The front and rear waist regions 6, 7 respectively have transversely opposite side edge regions joined together along welded zones 9 so as to define a waist-hole 11 and a pair of leg-holes 12. The cover 2 is formed of a laminated sheet composed of a liquid-impervious plastic film 13 and a nonwoven fabric 14. Elastic members 16, 17 respectively extend along peripheral edge regions of the waist-hole 11 and the leg-holes 12 in a circumferential direction and are secured under tension to the inner surface of the film 13 and/or the nonwoven fabric 14. The pad 3 extends along the inner surface of the cover 2 across the crotch region 8 to waist-opening peripheral edge regions of the front and rear waist regions 6, 7.

Figure 2:
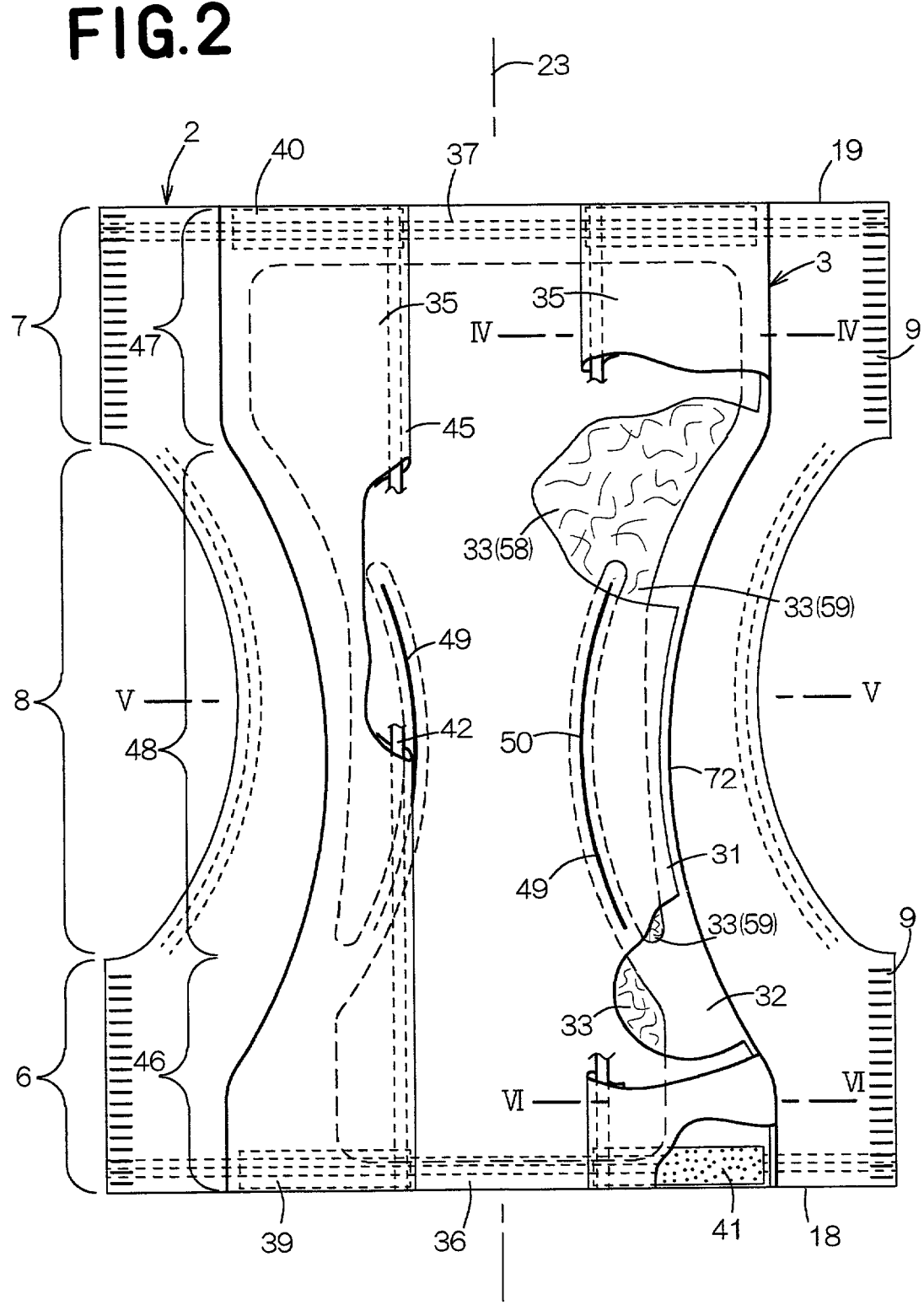
FIG. 2 is a partially cutaway plan view showing the wearing article.

FIG. 2 is a partially cutaway plan view showing the diaper 1 as pulled to opposite directions shown by arrows 21, 22 so as to separate the front and rear waist regions of the cover 2 along the welded zones 9. The cover 2 is hourglass-shaped and transversely opposite side edge regions in the crotch region 8 curve inwardly in a shape of circular arcs. Longitudinal center line of the pad 3 extending between the waist-hole peripheral edge regions of the cover 2 lies on a center line 23 bisecting a width of the cover 2.

The pad 3 comprises a liquid-pervious topsheet 31 facing the wearer's body, a liquid-impervious backsheet 32 facing the cover 2 and a liquid-absorbent core 33 disposed between these sheets 31, 32. The topsheet 31 and the backsheet 32 respectively form parts of a casing for covering the core 33. The pad 3 has front and rear waist regions 46, 47 and a crotch region 48. Between the waist-hole peripheral edge regions 18, 19, dimensions of these regions 46–48 are substantially in conformity with those of the corresponding regions 6–8. The top- and backsheets 31, 32 extend outwardly beyond an outer peripheral edge of the core 33 and are water-tightly joined together in these extensions to form longitudinally opposite end flaps 36, 37 and transversely opposite side flaps 35 around the outer peripheral edge of the core 33. The longitudinally opposite end flaps 36, 37 are joined to the inner surfaces of the respective waist-hole peripheral edge regions 18, 19 of the cover 2 by means of adhesive 70 (See FIG. 3) and the side flaps 35 are folded back toward the inner surface of the pad 3 (See FIG. 4). Longitudinally opposite end regions 39, 40 of the side flaps 35 are joined to the inner surface of the pad 3 by means of hot melt adhesive 41 and intermediate regions of the side flaps 35 defined between the end regions 39, 40 thereof are not joined to the inner surface of the pad 3. Inner side edge regions 45 of the respective side flaps 35 are folded back to form tubular spaces extending in parallel to the center line 23 and elastic members 42 extending also in parallel to the center line 23 are secured under tension to the inner surfaces of the respective tubular spaces (See FIG. 5). In the crotch region 48, the pad 3 is formed with a pair of darts 49 transversely opposite to each other about the center line 23 so that these darts curve toward the center line 23 in a shape of circular arcs.

The core 33 also is substantially hourglass-shaped and, in the crotch region 48, divided into a central core section 58 lying between the pair of darts 49 and a pair of lateral core sections 59 lying outside the respective darts 49. These central and lateral core sections 58, 59 extend forward and rearward beyond longitudinally opposite ends of the respective darts so that the central core section 58 has its width gradually enlarged toward the rear waist region 47 until the central core section 58 is joined with the lateral core sections 59 in a rearward region near the rear waist region 47 of the pad 3 while the central core section 58 is separated from the lateral core sections 59 in a front region near the front waist region 46 of the pad 3.

Figure 3:
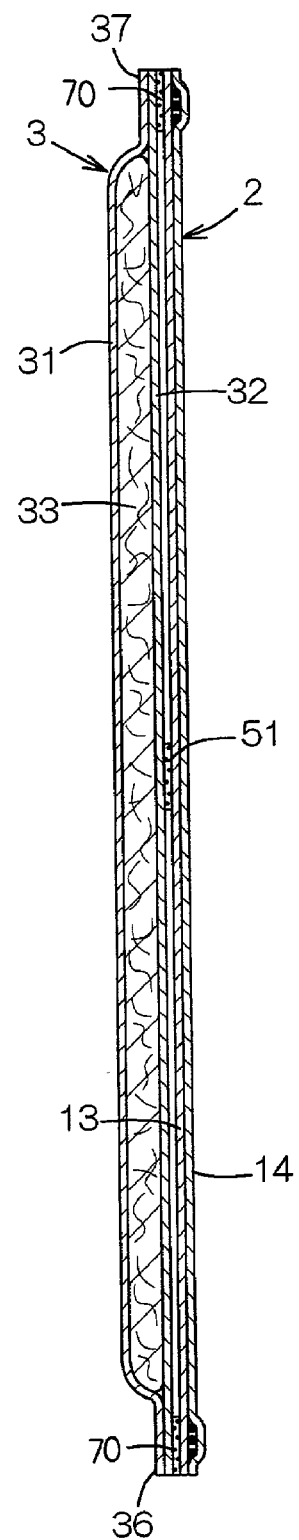
FIG. 3 is a cross-sectional view taken along a longitudinal center line in FIG. 2.

FIG. 3 is a cross-sectional view taken along the center line 23 in FIG. 2. As shown, the cover 2 comprises the film 13 and the nonwoven fabric 14 intermittently bonded to each other by a means of adhesive or welding (both not shown). In the pad 3, the topsheet 31 and the backsheet 32, which extend outwardly beyond the longitudinally opposite ends of the core 33, form the front and rear end flaps 36, 37. The pad 3 is joined to the cover 2 not only at the end flaps 36, 37 by means of adhesive 70 but also at locations on the center line and other appropriate locations thereof by a means of adhesive 51.

Figure 4:
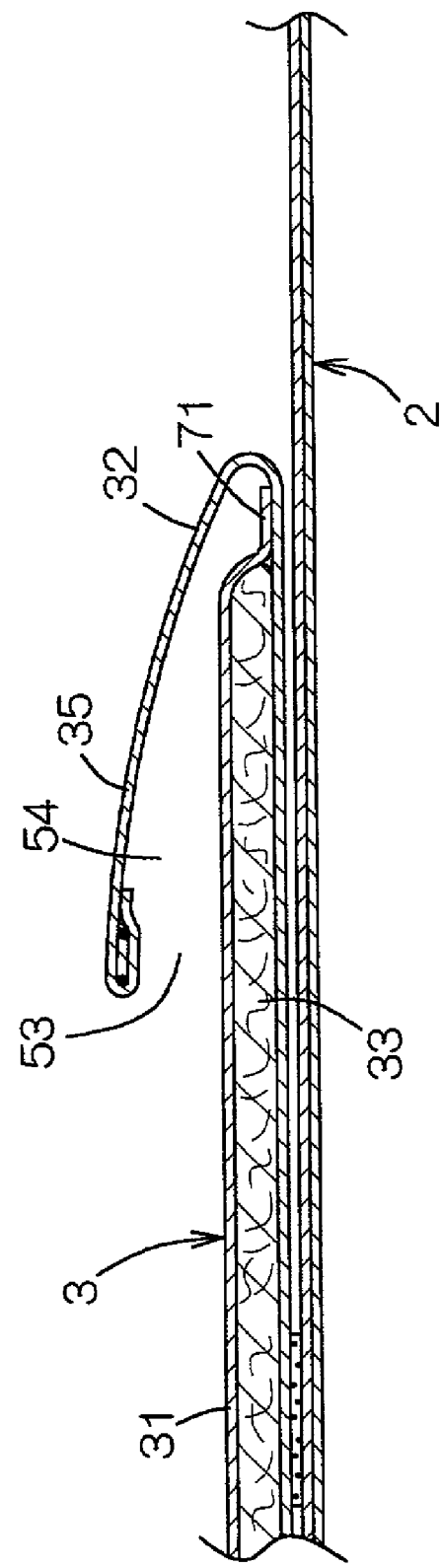
FIG. 4 is a cross-sectional view taken along a line IV—IV in FIG. 2.
Figure 5:
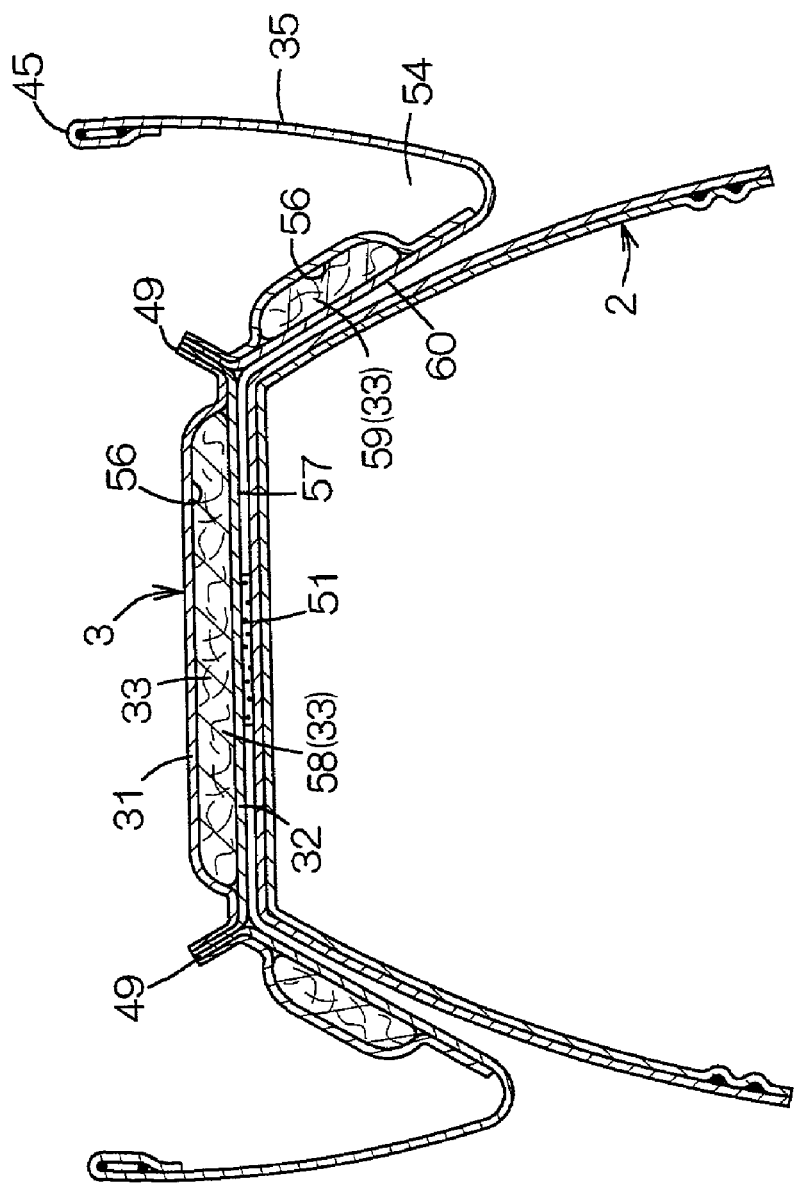
FIG. 5 is a cross-sectional view taken along a line V—V in FIG. 2.
Figure 6:
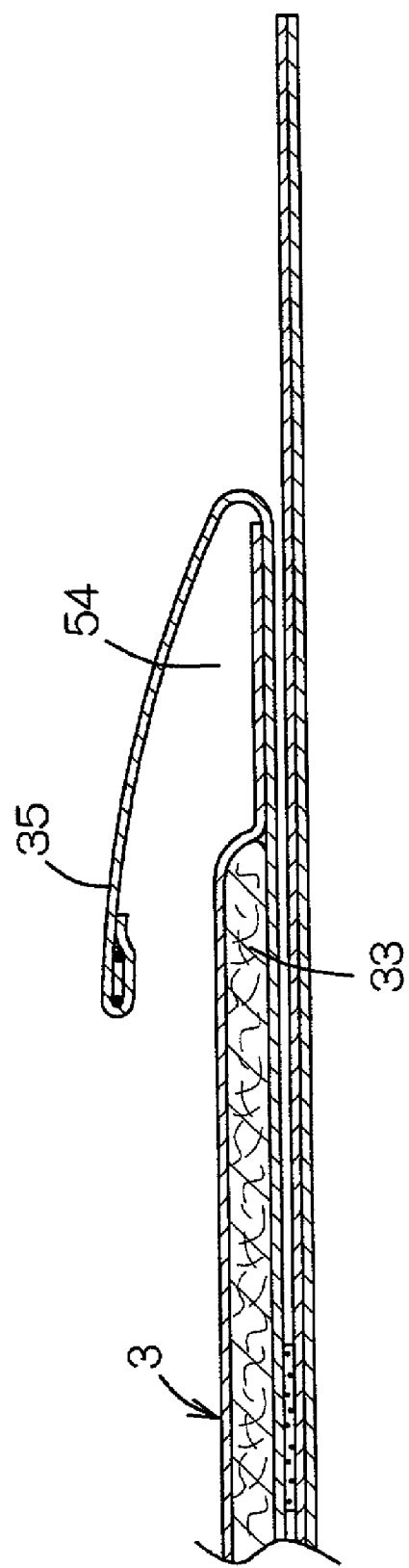
FIG. 6 is a cross-sectional view taken along a line VI—VI in FIG. 2.

FIGS. 4–6 are cross-sectional views taken along lines IV—IV, V—V and VI—VI, respectively, in FIG. 2. The line V—V corresponds to a center line bisecting the longitudinal length of the pad 3. As is seen in FIG. 4, the top- and backsheets 31, 32 of the pad 3 extend beyond the peripheral edge of the core 33 and are overlaid and bonded to each other. The backsheet 32 further extends outwardly beyond the topsheet 31 to form a major part of the side flaps 35. These side flaps 35 are folded back inwardly of the pad 3 so as to extend above the core 33 and thereby to form a pair of pockets 54 having openings 53 directed inward.

Referring to FIG. 5, in the respective darts 49 formed on the pad 3, the lower surfaces 56, 57 of the top- and backsheets 31, 32 covering the central core section 58 lying between the pair of darts 49, 49 and the lower surfaces 56, 57 of the top- and backsheets 31, 32 covering the lateral core sections 59 lying outside the region of the darts 49, are respectively overlaid with the lower surfaces facing each other and joined together by means of adhesive or welding. In the crotch region 48, the central core section 58 and the lateral core sections 59 constituting the core 33 are separated each other in the transverse direction of the pad 3 with the respective darts 49 therebetween (See FIG. 2). The top- and backsheets 31, 32 covering the respective lateral core sections 59 extend outwardly beyond the side edges of these lateral core sections 59 comprising a portion of the side edges of the core 33 and joined together. The backsheet 32 further extends outwardly beyond the side edges so as to constitute a major part of the side flaps 35. In the crotch region 48 of such pad 3, side edge regions 60 of the pad 3 including the lateral core sections 59 tend to hang down obliquely from the central core section 58 with the darts 49 composed of the overlaid sheets and functioning as hinge joints, if the core section 58 is in a horizontal state as is shown in FIG. 5. The side flaps 35, on the other hand, are folded back in the vicinity of outermost side edges of the respective lateral core sections 59 so as to extend obliquely upward and the pockets 54 also extend obliquely upward.

The darts 49 functioning in this manner may be obtained by, in the crotch region 48 of the pad 3, drawing the contour of the transversely opposite side regions of the top- and backsheets 31, 32 toward the center line 23 in a shape of circular arcs as is seen in FIG. 2 and joined the top- and backsheets 31, 32 along these circular arcs as is shown in FIG. 5. The darts 49 in a shape of circular arcs have respectively apices 50 adjacent to the center line 23. In a preferred embodiment of the pad 3, the inner side edge regions 45 of the respective side flaps 35 are positioned above the respective darts 49 in the vicinity of the apices 50 thereof so that the pockets 54 may be formed between the side flaps 35 and the lateral core sections 59, respectively. The pad 3 shown in FIG. 2 is formed with the darts 49 and consequently lines 72 along which the side flaps 35 are folded back in a shape of circular arcs which are convex inwardly of the pad 3.

Formation of the pockets 54 by the side flaps 35 shown in FIG. 4 will be apparent from FIG. 6 also. It should be understood that the core 33 is narrower in the front waist region 46 of the pad 3 than that in the rear waist region 47 (See FIG. 2) and does not extend to the bottom of the pockets 54. While it is possible to dimension the width of the core 33 in the front waist region 46 to be as large as in the rear waist region 47, the width of the core 33 in the front waist region 46 may be dimensioned to be relatively narrow in order to prevent the front waist region 46 from becoming bulky.

Figure 7:
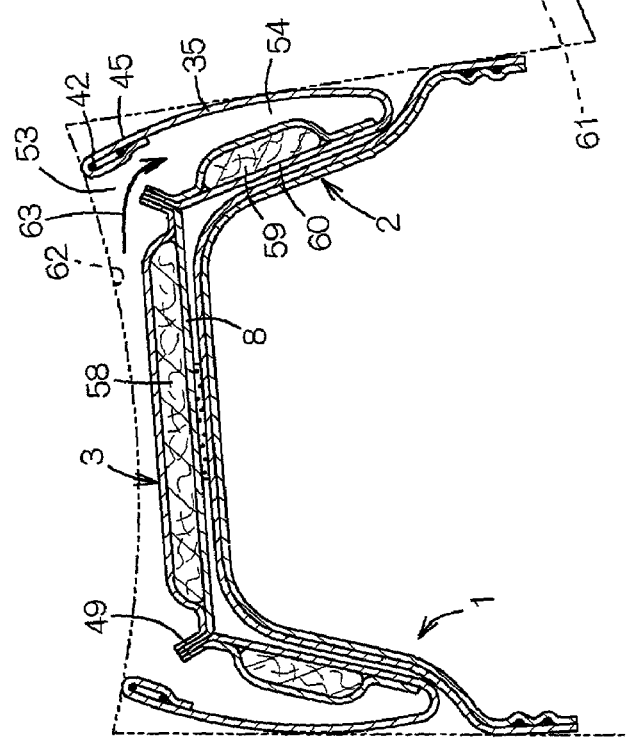
FIG. 7 is a cross-sectional view showing the wearing article as worn by its wear.

FIG. 7 is a cross-sectional view of the wearing article diagram schematically illustrating a state in which the diaper 1 has been worn and the crotch region 48 of the pad 3 comes in contact with the wearer's skin. The central core section 58 lying between the darts 49, 49 of the diaper 1 is placed against a region 62 defined between the wearer's groins 61 indicated by an imaginary line. The darts 49 extend toward the groins 61 and it will be apparent from FIG. 5 that the darts 49 function as the hinge joints about which the side regions 60 of the pad 3 including the lateral core sections 59 hang down obliquely along inner sides of the respective groins 61. The diaper 1 deforms itself in a curve along the wearer's body in a U-shape about the crotch region 8 upward toward the front and rear waist regions 6, 7 and thereupon contraction of the elastic members 42 associated with the respective side flaps 35 causes the side flaps 35 to uprise on the surface of the pad 3. In this way, the inner side edge regions 45 of the side flaps 35 are placed against the vicinity of the groins 61 from below. Thus the pockets 54 having the openings 53 are formed between the side flaps 35 and the lateral core sections 59. The central core section 58 is so dimensioned to be neatly positioned in the space defined between the groins of the thighs 61, in this sate of the diaper 1, without formation of many wrinkles. However, even if body fluids discharged on the diaper 1 can not be rapidly absorbed by the central core section 58 alone, the excessive quantity of the body fluids flows sideways as indicated by an arrow 63 into the pockets 54 and therefore it is not apprehended that such excessive quantity of body fluids might leak out from the diaper 1. The excessive quantity of body fluids is absorbed also by the lateral core sections 59 so that a limited absorbing capacity of the central core section 58 can be sufficiently compensated. As is apparent from FIG. 2, the lateral core sections 59 are contiguous to the central core section 58 in the rearward regions near the rear waist region 47 of the pad 3. Even if a relatively large quantity of body fluids flows into the pockets 54 and saturates the lateral core sections 59 with the fluids, the excessive quantity of body fluids permeates from the lateral core sections 59 to the region near the rear waist region 47 formulated to be relatively wide in dimension to absorb more quantity of the body fluids in the central core section 58. In this way, the quantity of body fluids which would be received by the pockets 54 can be decreased and thereby the lateral core sections 59 can maintain the absorbing capacity of the body fluids for a longer period of time.

The core 33 is divided in the crotch region 48 into the central core section 58 and the lateral core sections 59, so the side regions 60 of the pad 3 including the lateral core sections 59 are easily bent along the darts 49 and brought in close contact with the thighs. In addition, the central core section 58 is separated from the lateral core sections 59 also in the front region near the front waist region 46 so that the core 33 does not obstruct movement of the diaper wearer's legs. Without departing from the scope of this invention, it is possible to arrange the core 33 vice versa with respect to the illustrated embodiment so that the central core section 58 is contiguous to the lateral core sections 59 in the front region near the front waist region 46 and separated from the lateral core sections 59 in the rearward region near the rear waist region 47. It is also possible to arrange the core 33 so that the central core section 58 is contiguous to the lateral core sections 59 in the regions near the front and rear waist regions 46, 47, respectively.

Figure 8:
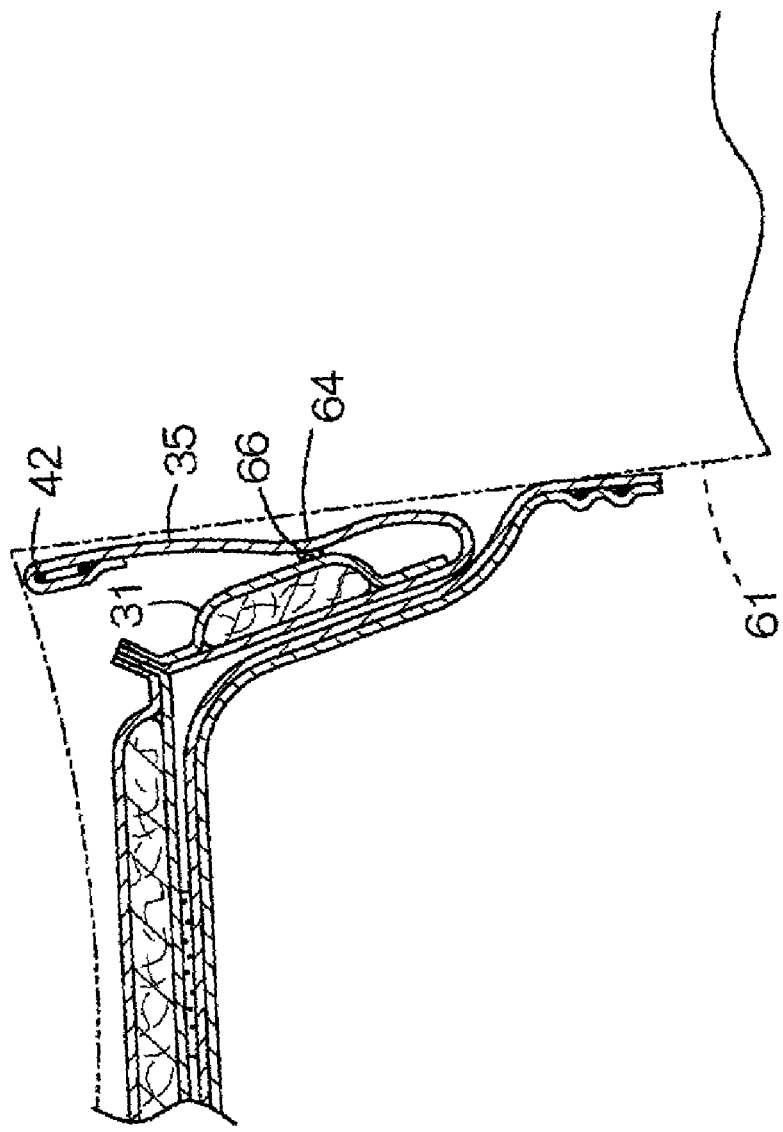
FIG. 8 is a view similar to FIG. 7 but showing another embodiment of this invention.

FIG. 8 is a view similar to FIG. 7 but partially showing another embodiment of this invention. According to this embodiment of this diaper 1, in the vicinity of the center line V—V (See FIG. 2) bisecting the longitudinal dimension of the pad 3, the inner surface of each side flap 35 is joined in a region 64 to the topsheet 31 covering each lateral core section 59 by means of adhesive 66 and this flap 35 is substantially upright above the region 64. If the side flaps 35 is in the state shown in FIG. 7, there is an anxiety that, depending on how the diaper 1 is worn, the side flaps 35 in the regions lower than the respective elastic members 42 might be slackened to reduce an inner volume of the respective pockets 54 and the slackened side flaps might prevent the body fluids from smoothly flowing into the pockets 54. Such anxiety can be reliably avoided by the side flaps 35 adapted to rise substantially upright between the elastic members 42 and the regions 64.

According to this invention, the means to retain the pad 3 against the wearer's body is not limited to the cover 2 of pants-type used in the illustrated embodiment. For example, waist belt may be used as a retaining means and front and rear end regions 36, 37 may be attached to this belt. In the case of pants-type cover 2, it is also possible to form the entire pants either by a liquid-pervious sheet or by a liquid-impervious sheet. While the side flaps 35 of the pad 3 in the illustrated embodiment have proximal end regions 71 (See FIG. 4) formed by the top- and backsheets 31, 32 and the remaining regions formed by the backsheet 32 alone, it is also possible to form the side flaps 35 by a sheet prepared separately of the top- and backsheets 31, 32 and bonded to any one of these top- and backsheets 31, 32. These side flaps 35 are preferably liquid-impervious.

The disposable body fluid absorbent wearing article according to this invention is characterized in the arrangement such that the parts of the liquid-absorbent core lying outside the darts formed on both side regions of the body fluid absorbent pad hang down so as to extend along the wearer's legs and these parts cooperate with the side flaps to form the pockets opening inwardly of the pad. This unique arrangement enables body fluids to be rapidly absorbed by the core although the core is dimensioned to be relatively narrow in the crotch region so that the core can be brought in close contact with the wearer's skin between the groins of the thighs without formation of many wrinkles. The core comprises the central core section lying between the darts and the lateral core sections lying outside the respective darts which are continuous to each other in the region beyond forward or rearward the darts. Such unique arrangement allows the quantity of body fluids by the lateral core sections lying outside the respective darts to spread to the relatively wide central core section. In this way, the lateral core sections can maintain an absorbing capacity of the body fluids for a longer period of time.

What is claimed is:

1. A disposable body fluid absorbent wearing article having a front waist region, a rear waist region and a crotch region, said article comprising:

a body fluid absorbent pad including a liquid-absorbent core;

a casing covering at least a body facing side of said absorbent core and extending outwardly from a circumferential edge of said core;

means for holding said body fluid absorbent pad on a wearer's body;

said pad being provided, at transversely opposite sides thereof and in said crotch region, with a pair of darts formed by folded parts of said casing, wherein said darts are opposed to each other and describe circular arcs which are convex toward a center line bisecting a width of said pad;

said core including a central core section lying between said darts and lateral core sections lying outside the respective darts, wherein said central and lateral core sections are contiguous to each other in at least one of regions beyond which are located beyond and forward and rearward, respectively, of said darts in a longitudinal direction of said pad; and the circumferential edge of said core being surrounded by end flaps and side flaps both being contiguous to a sheet of said casing and extending outward beyond the circumferential edge of said core;

wherein said side flaps extending outward beyond transversely opposite side edges of said core are folded back toward a body facing surface of said pad and longitudinally opposite end regions of said side flaps are bonded to said body facing surface so that pockets opening inwardly of said pad are formed between respective said side flaps and respective said lateral core sections; and said side flaps being folded back toward the body facing surface of said pad respectively have inner side edge regions which are provided, in parallel to said center line, with elastic members secured under tension to said inner side edge regions.

2. The wearing article according to claim 1, wherein said casing comprises at least a liquid-permeable topsheet defining the body facing surface of said absorbent pad.

3. The wearing article according to claim 1, wherein said casing comprises a liquid-permeable topsheet and a liquid-impermeable backsheet, and said core is disposed between said topsheet and backsheet.

4. The wearing article according to claim 1, wherein said central core section has a width increasing gradually from the region in which said central and lateral core sections become contiguous to each other toward one of front and rear ends of said core.

5. The wearing article according to claim 1, wherein the inner side edge regions of said side flaps, which are folded back toward the body facing surface of said pad, lie respectively in the vicinity of innermost points of the circular arcs.

6. The wearing article according to claim 1, wherein said side flaps, which are folded back toward the body facing surface of said pad, are joined, in middle regions between said longitudinally opposite end regions, to body facing surfaces of the lateral core sections.

7. The wearing article according to claim 1, wherein at least front and rear regions of said absorbent pad are joined integrally with said means.

8. The wearing article according to claim 1, wherein said means include a pants-type cover formed of a laminated sheet composed of a liquid-impervious plastic film and a nonwoven fabric.

9. A disposable body fluid absorbent wearing article, comprising:

a body fluid absorbent pad which includes a liquid-absorbent core and a sheet covering at least a surface of said absorbent core, said pad having a front region, a rear region and a crotch region extending in a longitudinal direction of said pad between said front and rear regions; and a cover for holding said pad on a wearer's body;

wherein said pad is provided, at transversely opposite sides thereof and in said crotch region, with a pair of darts formed at least by said sheet;

said core includes, in the crotch region, a central core section lying between said darts and lateral core sections each being separated from the central core section by one of said darts; and said central and lateral core sections are continuous to each other in at least one of the front and rear regions of said pad.

10. The article of claim 9, wherein said darts extend along two lines extending longitudinally of said pad, said lines being spaced apart from each other by a distance increasing from a minimum at a longitudinally middle point thereof to a maximum at longitudinally opposite ends thereof.

11. The article of claim 10, further comprising side flaps which extend outward beyond transversely opposite side edges of said core, wherein said side flaps are folded back toward an upper surface of said pad and have front and rear longitudinally opposite end portions being joined to the upper surface of said pad so that a pair of pockets opening inwardly of said pad are formed between respective said side flaps and respective said lateral core sections; and said side flaps, which are folded back toward the upper surface of said pad, are provided along inner side edge portions thereof with elastic members secured under extension to said inner side edge portions.

12. The article of claim 11, wherein the inner side edge regions of said side flaps, which are folded back toward the upper surface of said pad, lie respectively in the vicinity of apices of said darts.

13. The article of claim 11, wherein said side flaps, which are folded back toward the upper surface of said pad, are joined, in middle regions between said longitudinally opposite end regions, to the upper surface of said pad in regions above the respective lateral core sections.

14. The article of claim 10, wherein said darts describe circular arcs convex toward a longitudinal center line of said pad.

15. The article of claim 9, wherein said sheet is a liquid-permeable topsheet, said pad further comprises a liquid-impermeable backsheet, and said core is disposed between said topsheet and backsheet.

16. The article of claim 9, wherein said central core section has a width increasing gradually from a longitudinally middle zone of said crotch region toward the region in which said central and lateral core sections become contiguous to each other.

17. The article of claim 9, wherein at least one of said front and rear regions of said pad is joined to said cover.

18. The article of claim 9, wherein said cover is a pants-type cover formed of a laminated sheet comprising a liquid-impervious plastic film and a nonwoven fabric.

19. A disposable body fluid absorbent pad, comprising a liquid-absorbent core and a sheet covering at least a surface of said absorbent core, said pad having a front region, a rear region and a crotch region extending in a longitudinal direction of said pad between said front and rear regions, wherein said pad is provided, at transversely opposite sides thereof and in said crotch region, with a pair of darts formed at least by said sheet;

said core includes, in the crotch region, a central core section lying between said darts and lateral core sections each being separated from the central core section by one of said darts; and said central and lateral core sections are continuous to each other in at least one of the front and rear regions of said pad.

20. The pad of claim 19, wherein said darts extend along two lines extending longitudinally of said pad, said lines being spaced apart from each other by a distance increasing from a minimum at a longitudinally middle point thereof to a maximum at longitudinally opposite ends thereof.

21. The pad of claim 19, further comprising side flaps which extend outward beyond transversely opposite side edges of said core, wherein said side flaps are folded back toward an upper surface of said pad and have front and rear longitudinally opposite end portions being joined to the upper surface of said pad so that a pair of pockets opening inwardly of said pad are formed between respective said side flaps and respective said lateral core sections; and said side flaps, which are folded back toward the upper surface of said pad, are provided along inner side edge portions thereof with elastic members secured under extension to said inner side edge portions.

22. The pad of claim 21, wherein said side flaps, which are folded back toward the upper surface of said pad, are joined, in middle regions between said longitudinally opposite end regions, to the upper surface of said pad in regions above the respective lateral core sections.

\* \* \* \* \*